(12) United States Patent
Seo

(10) Patent No.: US 8,381,575 B2
(45) Date of Patent: Feb. 26, 2013

(54) SENSOR FOR HUMIDITY AND MANAGEMENT SYSTEM THEREFOR

(76) Inventor: Se Yeol Seo, Yongin-si (KR)

( * ) Notice: Subject to any disclaimer, the term of this patent is extended or adjusted under 35 U.S.C. 154(b) by 442 days.

(21) Appl. No.: 12/596,529

(22) PCT Filed: Apr. 18, 2008

(86) PCT No.: PCT/KR2008/002198
§ 371 (c)(1),
(2), (4) Date: Oct. 19, 2009

(87) PCT Pub. No.: WO2008/130149
PCT Pub. Date: Oct. 30, 2008

(65) Prior Publication Data
US 2010/0058835 A1    Mar. 11, 2010

(30) Foreign Application Priority Data
Apr. 19, 2007   (KR) ......................... 10-2007-0038443

(51) Int. Cl.
*G01N 19/10*    (2006.01)
(52) U.S. Cl. ....................................... 73/29.02
(58) Field of Classification Search ................. 73/29.02
See application file for complete search history.

(56) References Cited

U.S. PATENT DOCUMENTS

| | | | |
|---|---|---|---|
| 4,653,491 A | | 3/1987 | Okada et al. |
| 5,387,329 A | * | 2/1995 | Foos et al. ................ 204/403.06 |
| 5,503,719 A | * | 4/1996 | Foos et al. .................. 205/782.5 |
| 5,518,601 A | * | 5/1996 | Foos et al. ..................... 204/415 |
| 6,563,218 B2 | * | 5/2003 | Matsunaga et al. ........... 257/758 |
| 6,750,138 B2 | * | 6/2004 | Matsunaga et al. .......... 438/623 |
| 2004/0095247 A1 | | 5/2004 | De Haan et al. |

FOREIGN PATENT DOCUMENTS

| | | |
|---|---|---|
| DE | 1937858 | 2/1971 |
| DE | 3045514 | 7/1982 |
| DE | 4014213 | 11/1991 |
| DE | 10144022 | 3/2003 |
| DE | 69902660 | 4/2003 |
| JP | 2006-102039 | 4/2006 |
| JP | 2006-308502 | 11/2006 |
| KR | 10-2002-82593 | 10/2002 |
| KR | 10-2004-36321 | 4/2004 |

* cited by examiner

*Primary Examiner* — Hezron E. Williams
*Assistant Examiner* — Rodney T Frank
(74) *Attorney, Agent, or Firm* — Christopher Paul Mitchell

(57) ABSTRACT

The present invention relates to a sensor for humidity, etc. which has high precision, very small electrical power consumption and simplified composition, and a management system therefor. The sensor and the management system therefor according to the present invention are also economical. The sensor according to the present invention comprises two electrode pads and an absorption layer for absorbing moisture, etc. between them, and detects a capacitance variation and a resistance variation between the electrode pads, measuring humidity, etc. in real time. In the sensor, one or both of the electrode pads can be made by printing or coating a conductive material on a paper pad or a fabric pad in a mesh shape of fine lines. Or the electrode pads can be fabrics with fine thread of a mesh-type electric conductor coated by an absorptive material having an insulating property.

13 Claims, 3 Drawing Sheets

[Fig. 1]
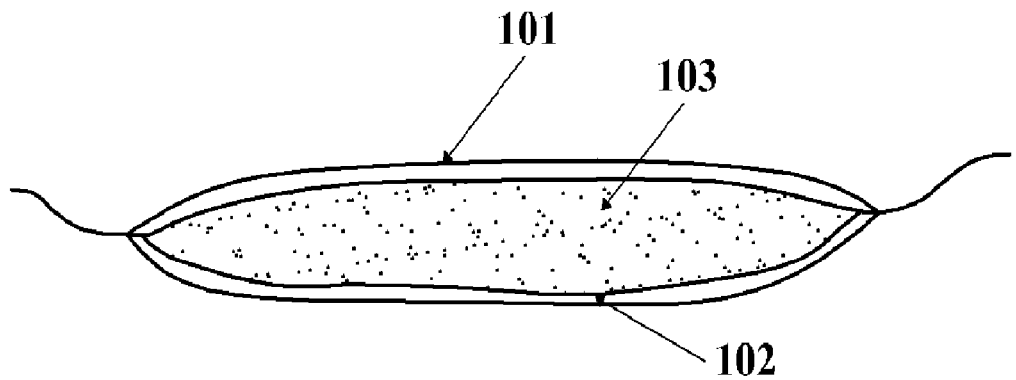
[Fig. 2]
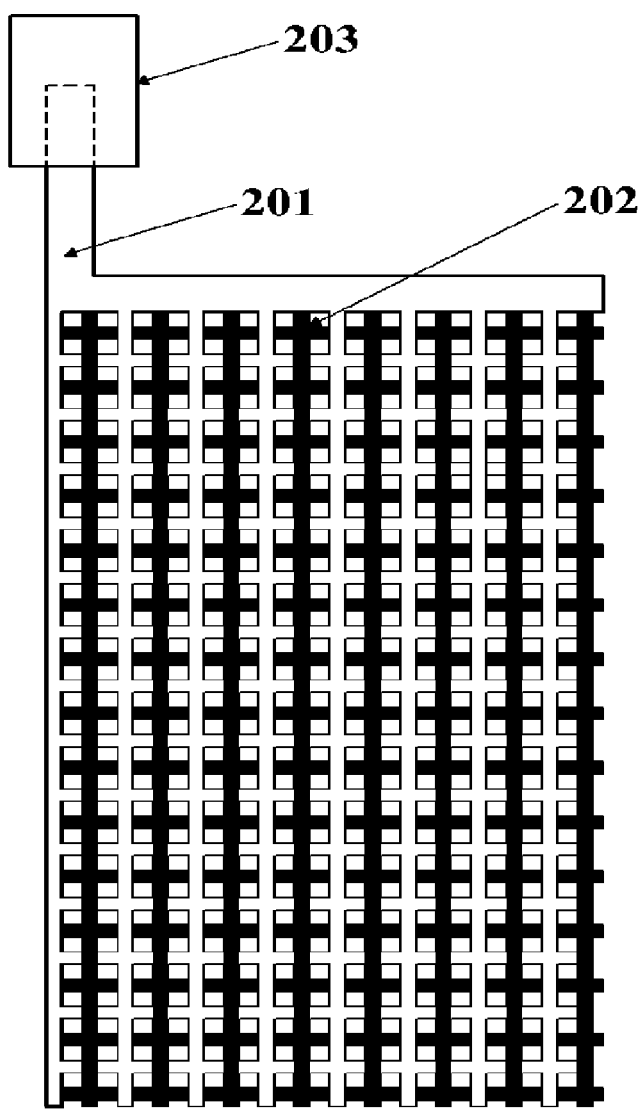

[Fig. 3]
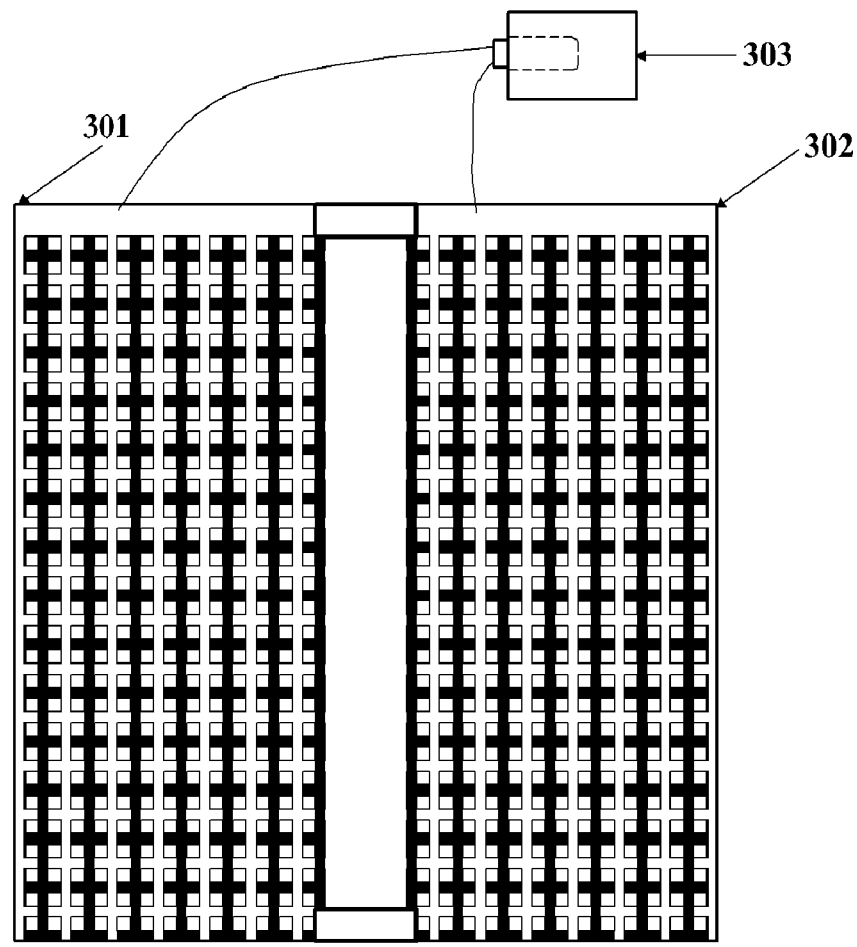
[Fig. 4]
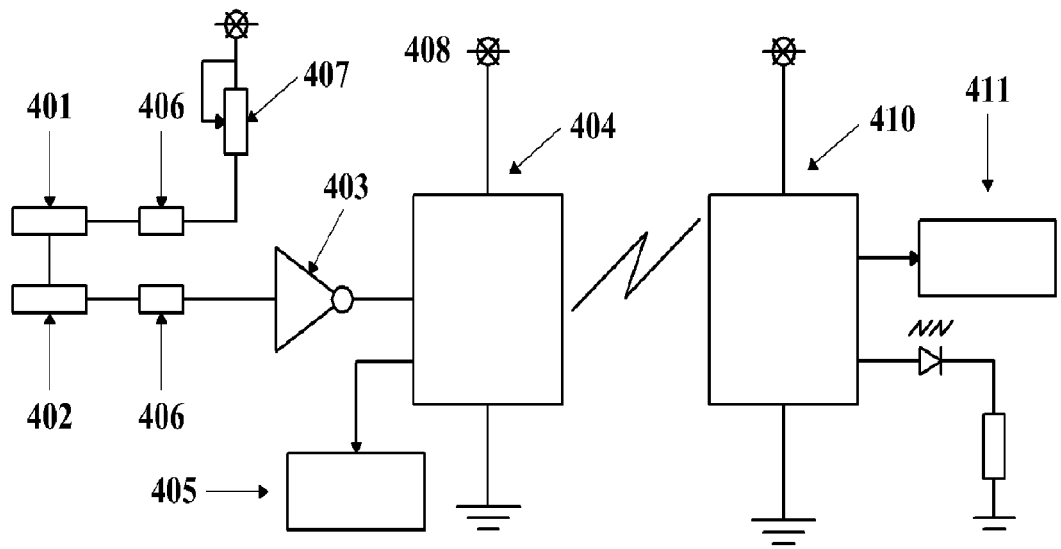

[Fig. 5]
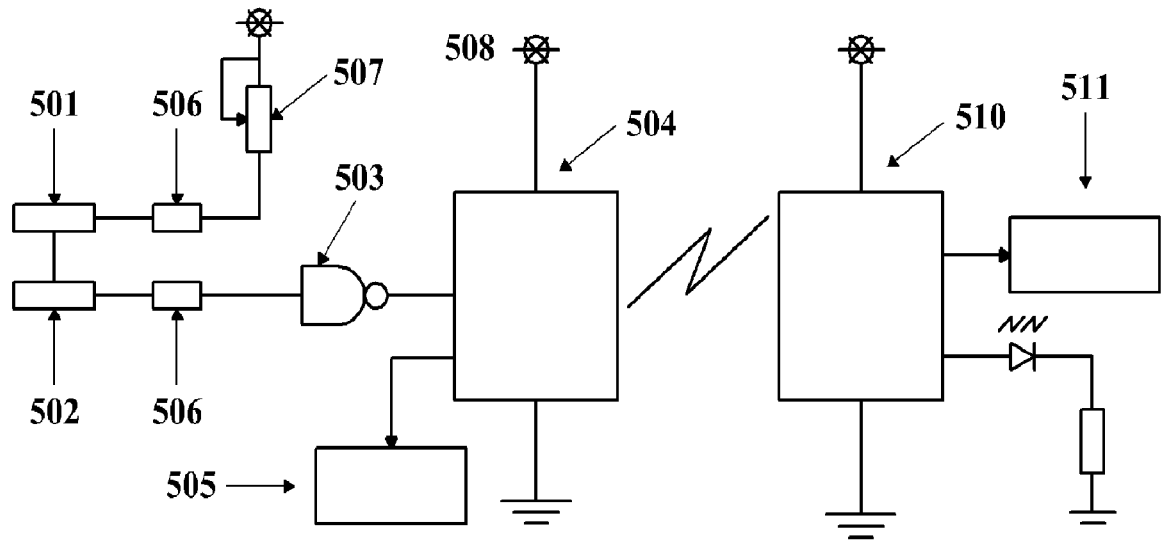
[Fig. 6]
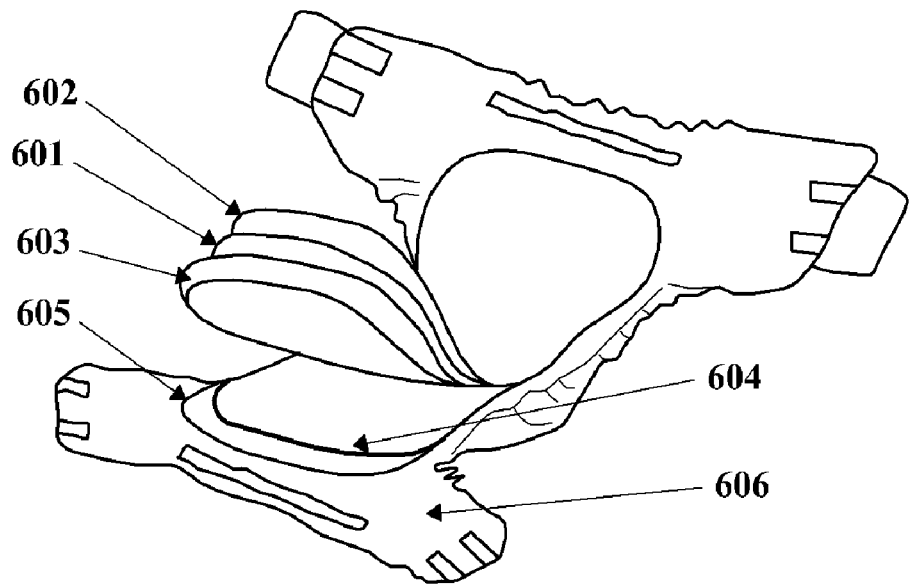

SENSOR FOR HUMIDITY AND MANAGEMENT SYSTEM THEREFOR

RELATED APPLICATIONS

This application is a 371 application of International Application No. PCT/KR2008/002198, filed Apr. 18, 2008, which in turn claims priority from Korean Patent Application Nos. 10-2007-0038443, filed Apr. 19, 2007, both of which are incorporated herein by reference.

TECHNICAL FIELD

The present invention relates to a sensor for humidity, etc. using a capacitance variation or a resistance variation and a management system therefor, and more specifically, it relates to a sensor for humidity, etc. which incorporates a flexible and water-permeable electrode pad, thereby having high precision, very small electrical power consumption and simplified composition, and a management system therefor.

BACKGROUND ART

In the field of humidity sensors which the present invention can be applied to, humidity sensors are classified into, according to the operation principles, a resistance sensor using a conductivity varied by moisture in porous ceramics or electrolytes, and a capacitive sensor using a permittivity (dielectric constant) variation generated when moisture is absorbed in a high-molecular polymer.

The resistance type humidity sensor is facilitated to be miniaturized and can be used in the wide range of humidity, and its response rate is fast. The capacitance type humidity sensor is made using the principle that capacitance varies with an amount of water absorbed in polymer material. The capacitance type humidity sensor has a wide humidity measuring range of 1 to 100% and it has a linear output so application circuits can be simply implemented. And also, in the area of measurement and adjustment, the capacitance type humidity sensor can work not only at room temperature but also at a temperature of −40° C. to 100° C. without a separate temperature-compensating apparatus. Further, the capacitance type humidity sensor can be easily applied to a microcomputer-utilizing circuit since it can operate on the direct current.

However, the conventional capacitance type humidity sensors, which are limited only for the microelement manufacturing field, are very expensive. Accordingly, they are not suitable for uses in agriculture, fisheries, forestry, medical treatment, hygiene and industrial fields.

In addition, in case of the field of detecting sensors for diapers, which the humidity sensor of the present invention can be used for, conventional detecting sensors for diapers generally include thin electrode films (aluminum films), that are conductive material, adhered in a given interval on a silicon or synthetic resin sheet to make a band shape. In this configuration, urine serves as a conductor which connects the electrode films electrically, and thus a urine detecting signal is detected.

The techniques for detecting urine or feces in a diaper and transmitting an alarm for the time to replace diapers have been widely proposed. However, the conventional techniques have many restrictions in materially manufacturing and putting to practical use due to a high manufacturing cost and malfunction. And the conventional techniques can be used for detecting urine by electric currents made by ions, etc., but have difficulties in detecting feces. Also, the conventional techniques have the important problem of possibly causing a sudden stimulus to a human body, since they use flow of electric currents. In other words, a voltage high enough to affect a human body can be applied between the electrodes, and urine can cause a high and abrupt electric current to flow between the electrodes, giving a sudden stimulus to a human body.

DISCLOSURE OF INVENTION

Technical Problem

Accordingly, the present invention has been made in view of the above problems occurring in the prior art, and it is an object of the present invention to provide a humidity sensor and management system therefor which have high precision, very small electrical power consumption and simplified composition and are also economical and appropriate to use for agriculture, fisheries, forestry, medical treatment, hygiene and industrial fields.

Another object of the present invention is to provide a diaper management system which has a high precision and very small electrical power consumption and is economical and can also detect both urine and feces with a high precision and has no stimulus for a human body.

Technical Solution

The above object of the present invention can be achieved by a humidity sensor comprising: two electrode pads having a water permeability and conductivity; an absorption layer for absorbing moisture, the absorption layer being disposed between the two electrode pads; and a sensing unit for detecting humidity through a capacitance variation between the two electrode pads.

The above object of the present invention can also be achieved by a humidity sensor comprising: two electrode pads having a water permeability and conductivity; an absorption layer for absorbing moisture, the absorption layer being disposed between the two electrode pads; and a sensing unit for detecting humidity through a resistance variation between the two electrode pads.

It is preferable that the two electrode pads of the present invention further include a connection terminal (line) composed of a conductive material wound with a soft material.

It is preferable that the two electrode pads of the present invention are arranged to be an upper layer and a lower layer, or a right layer and a left layer.

The electrode pads of the present invention are preferably water-permeable electrode pads with a thickness ranging from 0.02 mm to 0.06 mm.

One or both of the electrode pads of the present invention are preferably fabrics made by mixing or braiding thread and fine thread of an electric conductor.

One or both of the electrode pads of the present invention are preferably made by combining fine thread of a mesh-type electric conductor to a paper pad.

One or both of the electrode pads of the present invention are preferably made by printing or coating a conductive material on a fabric pad in a mesh shape of fine lines.

One or both of the electrode pads of the present invention are preferably made by printing or coating a conductive material on a paper pad in a mesh shape of fine lines.

One or both of the electrode pads of the present invention are preferably fabrics made of fine thread of a mesh-type electric conductor.

One or both of the electrode pads of the present invention are preferably fabrics made of fine thread of a mesh-type electric conductor coated by an absorptive material having an insulating property.

It is preferable that the humidity sensor of the present invention further includes a display unit for receiving and showing a humidity signal detected by the sensing unit.

And it is preferable that the humidity sensor of the present invention further includes a transmitting unit for receiving a humidity signal detected by the sensing unit and transmitting the humidity signal to a receiving unit.

The above object of the present invention can be achieved by a management system for a humidity sensor, comprising: the humidity sensor according to claim 14; a receiving unit for receiving a humidity signal transmitted from the transmitting unit; and a management display unit for showing a humidity received by the receiving unit.

It is preferable that, in the management system for a humidity sensor, the transmitting units transmit identification signals respectively intrinsic to a plurality of the humidity sensors and the receiving unit distinguishes the plurality of the humidity sensors through the intrinsic identification signals and the management display unit sorts and shows humidity for each of the plurality of the humidity sensors.

In addition, the above object of the present invention can be achieved by a management system for a diaper, comprising: a detecting sensor for a diaper, which is the humidity sensor according to claim 14; a receiving unit for receiving a urination or stooling signal from the transmitting unit; and a management display unit for showing whether urination or stooling has been made or not according to the urination or stooling signal received by the receiving unit.

It is preferable that, in the management system for a diaper, the transmitting units transmit identification signals respectively intrinsic to a plurality of the humidity sensors and the receiving unit distinguishes the plurality of the humidity sensors through the intrinsic identification signals and the management display unit sorts and shows whether or not urination or stooling has been made for each of the plurality of the humidity sensors.

It is preferable that the management system for a diaper of the present invention further includes an alarm unit for informing whether urination or stooling has been made, through a speaker, a lamp, etc., when the urination or stooling signal is received by the receiving unit.

It is preferable that the management system for a diaper of the present invention further includes a transmitting unit for management, which informs a wired or wireless terminal of the urination or stooling signal.

Advantageous Effects

The humidity sensor or the detecting sensor for a diaper in accordance with the present invention has a simplified structure. And it has the advantageous effect of consuming very small electrical power, since it detects a capacitance variation or a resistance variation.

Also, the humidity sensor of the present invention functions with a high precision, since it uses electrode pads of high water-permeability to measure a capacitance variation or a resistance variation. For the reason, it is economical and it can have a structure appropriate for uses in many fields, such as agriculture, fisheries, forestry, medical treatment, hygiene and industries.

In addition, the detecting sensor for a diaper in accordance with the present invention has no effect to a human body and is very economical since a sensing unit and a transmitting unit and the like can be attached to and detached from a diaper. And it has the advantageous effect of giving no stimulus or harm to a human body or skin due to a soft and flexible pad, sensing unit and transmitting unit used in it.

BRIEF DESCRIPTION OF THE DRAWINGS

FIG. 1 is a simplified diagram illustrating electrode pads and an absorption layer between them which can be used for the humidity sensor and the detecting sensor for a diaper according to the present invention;

FIG. 2 is a constituent diagram of an electrode pad using fabrics in which thread and fine thread of an electric conductor are mixed or braided, according to the present invention;

FIG. 3 is a constituent diagram showing that electrode pads using fabrics in which thread and fine thread of an electric conductor are mixed or braided are arranged to be a right and a left layers, according to the present invention;

FIG. 4 is a schematic diagram presenting a humidity sensor and a management system for the humidity sensor, according to a first embodiment of the present invention;

FIG. 5 is a schematic diagram presenting a humidity sensor and a management system for the humidity sensor, according to a second embodiment of the present invention; and FIG. 6 is a constituent diagram illustrating a diaper equipped with a detecting sensor for a diaper according to an embodiment of the present invention.

DESCRIPTION ON MAIN REFERENCE NUMERALS 101, 102, 301, 302, 401, 402, 501, 502: electrode pad
103: absorption layer 201: fine thread of an electric conductor
202: thread 203, 303, 406, 506: connection terminal (line)
403: capacitance sensing unit 404, 504: transmitting unit
405, 505: display unit 407, 507: variable resistance
408, 508: power supply unit 410, 510: receiving unit
411, 511: management display unit 503: resistance sensing unit
601: inner electrode pad and absorption layer 602: inner cover
603: absorption sheet 604: outer electrode pad and absorption layer
605: waterproof cover 606: outer cover

MODE FOR THE INVENTION

The terms and the words used in the specification and the claims should not be limitedly construed with ordinary or lexical meaning. Rather, they should be construed with the meanings and the conceptions according to the idea of the present invention, abiding by the principle that an inventor can properly define the conception of terms so as to describe his or her own invention with the best manner.

While the present invention has been described with reference to particular illustrative embodiments, it is not to be restricted by the embodiments but only by the appended claims. It is to be appreciated that those skilled in the art can change or modify the embodiments without departing from the scope and spirit of the present invention.

Hereinafter, the preferred embodiments of the present invention will be described in detail with reference to the accompanying drawings.

FIG. 1 is a simplified diagram illustrating electrode pads and an absorption layer between them, which can be used for the humidity sensor and the detecting sensor for a diaper according to the present invention.

The present invention relates to a sensor having an absorption layer (103) which can absorb moisture, etc. between the mesh-type electrode pads (101 and 102) and detecting a capacitance variation or a resistance variation between the electrode pads. The sensor can be used to measure humidity or detect whether a diaper has been contaminated with urine or feces.

The mesh-type electrode pads in accordance with the present invention are fabrics made by mixing or braiding thread (202) and fine thread of an electric conductor (201), as shown in FIG. 2. And braiding thread and fine thread of an electric conductor means twisting them with each other to make a thread. Fabrics are woven with thus-made thread to form the electrode pads (101 and 102). At this time, various threads such as a synthetic fiber, cotton, etc. can be used for the thread, and aluminum alloy, copper, stainless steel alloy, etc. can be used for the fine thread of the electric conductor. And also, gold or silver fine thread can be used as the case may be. In addition, the electrode pads (101 and 102) can be made using a paper, and at this time, the paper can be non-woven fabrics.

Or, the electrode pad can comprise a fabric made with only fine thread of an electric conductor. The electrode pad can comprise a fabric using fine thread of a mesh-type electric conductor coated by an absorptive material having an insulating property.

Or, the electrode pad can be made by printing or coating a conductive material to a fabric pad or a paper pad in a mesh shape of fine lines. When the conductive material is printed or coated, the fine lines can be formed to have a thickness, a width, intervals and a mesh shape, according to a user's needs or uses.

The electrode pads can have various thicknesses according to their uses. But it is preferable that the electrode pads (101, 102) themselves have a very thin thickness of 0.02 mm~0.06 mm, since a measurement target is a capacitance variation or a resistance variation in the absorption layer (103). And for the sensor of the present invention, both of the electrode pads can be made using a fabric or a paper, or one of the electrode pads can be made using a fabric and the other of the electrode pads can be made using a paper.

The absorption layer (103) is formed between the electrode pads, as shown FIG. 1. Any material which can absorb moisture can be used for the absorption layer (103). The thickness of the absorption layer (103) determines a distance between both the electrode pads and can be adequately controlled according to a use and accuracy of the sensor.

The electrode pads (101 and 102) can be disposed to be an upper layer and a lower layer with the absorption layer (103) between them. Or they can be disposed at the left side and the right side of the absorption layer (103).

FIG. 3 shows that the electrode pads same as that shown in FIG. 2 can be disposed to be at the left and right side of the electrode pads. Referring to FIG. 3, the electrode pads (301 and 302), which are paper pads or fabric pads, are arranged to be at the right and left sides of the absorption layer (103). In such a right and left arrangement, a moisture absorption sheet can be disposed on one or both sides of the electrode pads (301 and 302) so as to improve the function of detecting a capacitance variation or a resistance variation.

The electrode pads (101, 102, 301 and 302) in accordance with the present invention have water permeability as well as conductivity so moisture passing through the electrode pads (101, 102, 301 and 302) can be rapidly absorbed into the absorption layer (103) between the electrode pads. And since the electrode pads (101, 102, 301 and 302) are soft and flexible, the electrode pads can adhere closely to a measurement target, thus enabling more minute measurements.

The connection terminal (line) (203 and 303) is composed of a conductive material wound with a soft material so it is easily linked with the electrode pads (101, 102, 301 and 302) and a sensing unit or a transmitting unit.

The soft material can be made of synthetic resins harmless for a human body, such as polyvinyl chloride (PVC), silicon, sponge, etc.

More preferably, a conductive link unit wound with a soft material is further included in the connection terminal (line), making a more efficient link to the electrode pads (101, 102, 301 and 302) and the sensing unit or the transmitting unit.

Referring to FIG. 4, a capacitance sensing unit (403) measures a capacitance variation between the electrode pads, when the absorption layer (103) between the electrode pads absorbs moisture, etc. What the sensor according to the present invention is used for is determined according to the type of measured values obtained by the capacitance sensing unit (403). That is, if capacitance variations are minutely measured and continuously tracked, the sensor can be used as a humidity sensor. Meanwhile, if only a critical capacitance variation is detected, the sensor can be used as a detecting sensor for a diaper.

Referring to FIG. 5, a resistance sensing unit (503) measures a resistance variation between the both electrode pads, when the absorption layer (103) between the electrode pads absorbs moisture, etc. What the sensor according to the present invention is used for is determined according to the type of measured values obtained by the resistance sensing unit (503). That is, if resistance variations are minutely measured and continuously tracked, the sensor can be used as a humidity sensor. Meanwhile, if only a critical resistance variation is detected, the sensor can be used as a detecting sensor for a diaper.

The capacitance sensing unit (403) and the resistance sensing unit (503) can be used separately or simultaneously.

Referring to FIGS. 4 and 5, the signal corresponding to the result values detected by the capacitance sensing unit (403) or the resistance sensing unit (503) can be sent to and displayed in a display unit (405, 505) attached to the sensor. Or, the signal corresponding to the result values detected by the capacitance sensing unit (403) or the resistance sensing unit (503) can be sent to a transmitting unit (404, 504), and then displayed in a receiving device equipped with a receiving unit (410, 510), or can be informed by alarming through a speaker, a lamp, etc. At this time, the receiving unit (410, 510) receives the signal transmitted from the transmitting unit (404, 504). It must be noted that, despite their literal meanings, the receiving unit according to the present invention can transmit a signal for the sensor to make a performance and the transmitting unit can receive the signal. That is, the functions of the receiving unit and the transmitting unit are not limited by the literal terms used herein.

FIG. 4 is a schematic diagram presenting a humidity sensor and a management system for the humidity sensor, according to a first embodiment of the present invention. The sensor in accordance with the present invention comprises the electrode pads (401 and 402), the capacitance sensing unit (403), the transmitting unit (404), the display unit (405), the connection terminal (line) (406) connecting each of the electrode pads (401 and 402) with the sensing unit (403) or a power supply, a variable resistance (407) controlling sensitivity of the sensor, a power supply unit (408), etc. Moreover, the receiving unit (410) and the management display unit (411) are further included in the management system for the sensor.

FIG. 5 is a schematic diagram presenting a humidity sensor and a management system for the humidity sensor, according to a second embodiment of the present invention. The sensor of the present invention comprises the electrode pads (501 and 502), the resistance sensing unit (503), the transmitting unit (504), the display unit (505), the connection terminal (line) (506) connecting each of the electrode pads (501 and 502) to the sensing unit (503) or a power supply, a variable resistance (507) controlling sensitivity of the sensor, a power supply unit (508), etc. Moreover, the receiving unit (510) and the management display unit (511) are further included in the management system for the sensor.

The management system for a humidity sensor according to the first and the second embodiments of present invention comprises the humidity sensor, the receiving unit (410, 510) and a management display unit (411, 511). At this time, one or more than one humidity sensors can be used. And in case of plural humidity sensors, each of the transmitting units (404 and 504) of the plural humidity sensors has an intrinsic identification signal and, using the intrinsic identification signal, the receiving units (410 and 510) can tell what humidity sensor a signal comes from. The receiving unit (410, 510) to receive a signal from the humidity sensor can be installed with a management display unit (411, 511) to show the humidity value received by the receiving unit (410, 510). The management display unit (411, 511) determines what humidity sensor a signal comes from, through an identification signal intrinsic to each of the humidity sensors and displays humidity data from the corresponding humidity sensor. In addition, it is more preferable that a bidirectional or a unidirectional communication means are added to the receiving unit and the transmitting unit for preventing interference.

The management system for the humidity sensor according to the present invention can be used for, for example, a container for cultivating farm products, an apparatus for germinating seeds, a management system for stored or displayed agricultural and marine products, or an industrial seal facility in which very dry environment has to be maintained, in fisheries, forestry and all kinds of industrial fields. That is, the management system for the humidity sensor has a wide range of applications. Especially, the management system for the humidity sensor can be widely applied to a field of humidity management which requires an electrode pad made of fabric or paper materials and thus having good flexibility and water permeability. And also, the humidity sensor according to the present invention can be used as a detecting sensor for a diaper which determines whether a diaper wearer has made urination or stooling or not.

FIG. 6 is a constituent diagram illustrating a diaper equipped with a detecting sensor for a diaper according to an embodiment of the present invention. The inner electrode pad and absorption layer (601) of the detecting sensor are attached between the inner cover (602) and the absorption sheet (603) of a diaper. The waterproof cover (605) and the outer cover (606) are formed outside of the outer electrode pad and absorption layer (604). It is more preferable that the waterproof cover is positioned between the absorption sheet (603) and the outer electrode pad and absorption layer (604), unlike FIG. 6. And also, the electrode pad and the absorption layer of the detecting sensor for a diaper can be equipped on one or both of the upper and the lower sides of the absorption sheet (603), depending on uses of the diaper, such as for an infant, for a patient, etc. At this time, the diaper can be made so that a user can change the positions of the electrode pad and absorption layer.

The sensing unit connected with the electrode pad, the transmitting unit or the display unit is equipped on or near a diaper belt and can be formed to be separated from or connected to the electrode pad through a connection terminal (line). At this time, the position and shape of electrode pads can be varied with their applications. In case of a diaper wearer having made urination or stooling, the sensing unit detects a capacitance variation or a resistance variation between the electrode pads and sends a corresponding signal to the transmitting unit or display unit. The sensing unit can continuously or periodically detect whether a diaper wearer has made urination or stooling or not. Further, the detecting sensor for a diaper according to the present invention can have a built-in means for measuring for a lifetime of the power supply. So, when the power available is below a standard value, the detecting sensor for a diaper according to the present invention can send a corresponding signal to the transmitting unit or display unit.

The sensing unit, the display unit and the transmitting are wound with soft and flexible material which is harmless to a human body, so they do not cause any troubles to human skin when attached to a human body. And the sensing unit, the display unit and the transmitting unit can be made to have shapes proper to their uses.

A management system for a diaper can be made comprising the detecting sensor for a diaper according to the embodiment of the present invention and management devices therefor. The management devices for the detecting sensor for a diaper comprises a receiving unit to receive a urination or stooling signal from the transmitting unit and a management display unit to show whether urination or stooling has been made or not, according to the urination or stooling signal received by the receiving unit. The management system for a diaper according to the present invention can manage a plurality of the detecting sensors. At this time, each of the transmitting units of the plural detecting sensors has an intrinsic identification signal, and accordingly, the receiving unit in the management device can recognize what detecting sensor a signal comes from. The management device determines what detecting sensor a signal comes from, using the intrinsic identification signal of the received signal and then displays the information from the signal for the corresponding detecting sensor. And the management device can give the information from the signal by alarming through a speaker, a lamp, etc. Also, the management device can further comprise a transmitting unit for management, which can transmit a signal to a wired or wireless terminal of communication networks using a wired or wireless network, such as a pager of an external manager. Moreover, the management device in accordance with the present invention can store data of a urination or stooling signal according to their corresponding detecting sensors and utilize the data for a diagnosis.

Although the present invention has been described with reference to several preferred embodiments, the description is illustrative of the invention and is not to be construed as limiting the invention. Various modifications and variations may occur to those skilled in the art, without departing from the scope of the invention as defined by the appended claims.

INDUSTRIAL APPLICABILITY

The humidity sensor and the management system for the humidity sensor according to the present invention can be used for, for example, a container for cultivating farm products, an apparatus for germinating seeds, a management system for stored or displayed agricultural and marine products, or an industrial seal facility in which very dry environment has to be maintained, in fisheries, forestry and all kinds of industrial fields.

The humidity sensor and the management system for the humidity sensor according to the present invention can be widely applied to a field of humidity management requiring an electrode pad which is made of fabric or paper materials and fine thread or fine lines of an electric conductor, thus having good flexibility and water permeability.

In addition, the humidity sensor and the management system for the humidity sensor according to the present invention can be applied to sanitary care products or medical care products since the humidity sensor can be attached to a diaper and used to determine whether a diaper wearer has made urination or stooling or not.

The invention claimed is:

1. A humidity sensor for a diaper comprising:
   two electrode pads having water-permeability conductivity and flexibility, wherein the electrode pads are made by combining fine thread of a mesh-type electric conductor to a paper pad or are made by mixing thread and fine thread of an electric conductor;
   an absorption layer for absorbing moisture, the absorption layer being disposed between the two electrode pads; and
   a sensing unit for detecting humidity through a capacitance variation between the two electrode pads.

2. The humidity sensor for a diaper as recited in claim 1, wherein the two electrode pads comprise a connection terminal (line), the connection terminal (line) being composed of a conductive material wound with a soft material.

3. The humidity sensor for a diaper as recited in claim 1, wherein the two electrode pads are arranged to be an upper layer and a lower layer.

4. The humidity sensor for a diaper as recited in claim 1, wherein the two electrode pads are arranged to be a right layer and a left layer.

5. The humidity sensor for a diaper as recited in claim 1, wherein the electrode pads have a thickness ranging from 0.02 mm to 0.06 mm.

6. The humidity sensor for a diaper as recited in claim 1, wherein one or both of the electrode pads are made by printing or coating a conductive material on a fabric pad in a mesh shape of fine lines.

7. The humidity sensor for a diaper as recited in claim 1, wherein one or both of the electrode pads are made by printing or coating a conductive material on a paper pad in a mesh shape of fine lines.

8. The humidity sensor for a diaper as recited in claim 1, wherein one or both of the electrode pads are fabrics made of fine thread of a mesh-type electric conductor.

9. The humidity sensor for a diaper as recited in claim 1, wherein one or both of the electrode pads are fabrics made of fine thread of a mesh-type electric conductor, the fine thread of the mesh-type electric conductor being coated by an absorptive material having an insulating property.

10. The humidity sensor for a diaper as recited in claim 1, further comprising a display unit for receiving and showing a humidity signal detected by the sensing unit.

11. The humidity sensor for a diaper as recited in claim 1, further comprising a transmitting unit for receiving a humidity signal detected by the sensing unit and transmitting the humidity signal to a receiving unit.

12. A management system for a diaper, comprising;
   a humidity sensor for a diaper, which is according to claim 11 and is one or more;
   the transmitting unit, which, is one or more and transmits identification signals respectively intrinsic to a receiving unit;
   the receiving unit, which receives a urination or stooling signal from the transmitting unit and distinguishes the one or more humidity sensors through the intrinsic identification signals;
   a management display unit, which shows whether urination or stooling has been made or not according to the urination or stooling signal received by the receiving unit and whether urination or stooling has been made or not according to each the one or more humidity sensors;
   an alarm unit for informing whether urination or stooling has been made, through a speaker, etc., when, the urination or stooling signal is received by the receiving unit; and
   a transmitting unit for management, which informs a wired or wireless terminal of the urination or stooling signal received by the receiving unit.

13. The humidity sensor for a diaper as recited in claim 1, comprising one of the electrode pads and a waterproof layer positioned between the absorption layers.

* * * * *